(12) United States Patent
Fang

(10) Patent No.: US 7,438,937 B2
(45) Date of Patent: Oct. 21, 2008

(54) **TOPICAL BURN COMPOSITION CONTAINING *MENTHA HAPLOCALYX* AND ONE OR BOTH OF *ALOE VERA* AND RECOMBINANT HUMAN EPIDERMAL GROWTH FACTOR**

(76) Inventor: Changge Fang, 4849 Connecticut Ave., NW., Apt. #726, Washington, DC (US) 20008

( * ) Notice: Subject to any disclaimer, the term of this patent is extended or adjusted under 35 U.S.C. 154(b) by 252 days.

(21) Appl. No.: 11/297,399

(22) Filed: Dec. 9, 2005

(65) Prior Publication Data

US 2007/0134352 A1    Jun. 14, 2007

(51) Int. Cl.
*A61K 35/78*     (2006.01)
(52) U.S. Cl. ....................................... 424/744
(58) Field of Classification Search .................. 424/744
See application file for complete search history.

(56) References Cited

U.S. PATENT DOCUMENTS 6,419,936 B1   7/2002   Schmoyer

2005/0013821 A1   1/2005   Anton
2005/0164924 A1*  7/2005   Wong ........................... 514/12

FOREIGN PATENT DOCUMENTS

| JP | A 55-151514 | | 11/1980 |
| JP | 05025082 A | * | 2/1993 |
| JP | 05025083 A | * | 2/1993 |
| JP | A 10-236944 | | 9/1998 |
| JP | A 2000-044419 | | 2/2000 |
| JP | A 2001-081008 | | 3/2001 |

OTHER PUBLICATIONS

FuZhou Corona Science & Technology Develpment Co. Ltd. website page for extract of *Metha haplocalyx Briq.*, 2001.*
Tradekey website page, Hangzhou New Asia International Co. Ltd. Extract *Mentha haplocalyx Briq.* page, Jan. 2007.*

* cited by examiner

*Primary Examiner*—Ralph Gitomer
(74) *Attorney, Agent, or Firm*—Oliff & Berridge, PLC

(57) ABSTRACT

A topical burn composition containing an extract of *Mentha haplocalyx* Brig. and at least one of an extract of *Aloe vera* and recombinant human epidermal growth factor.

19 Claims, No Drawings

TOPICAL BURN COMPOSITION CONTAINING *MENTHA HAPLOCALYX* AND ONE OR BOTH OF *ALOE VERA* AND RECOMBINANT HUMAN EPIDERMAL GROWTH FACTOR

The present disclosure is directed to compositions and methods for treating damaged, such as burned, tissue or skin. More particularly, the present disclosure is directed to compositions comprising an extract of *Mentha haplocalyx* and at least one of an extract of *Aloe vera* and recombinant human epidermal growth factor, methods of making such compositions, and methods of using such compositions for treating damaged, such as burned, tissue or skin.

BACKGROUND

Topical skin treatments are known. Such treatments, and particularly compositions utilized in such treatments, have included a wide range of natural and synthetic substances, both as active and inactive ingredients.

For example, U.S. patent application Publication Ser. No. 2005/0013821 to Anton discloses a pharmaceutical composition for use as an active substance for topical application in the vicinity of a user's vulva or anus. The composition contains an emollient and an extract of one or more members of the Mint (Mentha) family.

The internet web site http://www.innvista.com/health/herbs/mint.htm discloses that Mint was used in England at least as early as the ninth century for healing skin ulcers. It further discloses that Mint can be used as a topical anesthetic, and can be used to treat skin irritations, burns, and inflammations.

U.S. Pat. No. 6,419,936 to Schmoyer discloses a topical skin ointment that includes ingredients to reduce the discomfort associated with minor skin irritations and to promote the natural healing process. The topical skin ointment includes the following ingredients: Vitamin E in an oil base, Vitamin A and Vitamin D ointments, Zinc Oxide ointment, and *Aloe Vera* extract.

In addition, various other skin preparations are known that contain extracts from one or more plants, such as *Mentha piperita, Mentha arvensis, Mentha viridis*, and *Mentha herba*. See, for example, Japanese Patent Application Publications Nos. 2000-44419, 2001-81008, 10-236944, and 55-151514.

SUMMARY

This disclosure describes a topical composition for treating tissue, such as skin, burns. The composition contains an extract of *Mentha haplocalyx*, and optionally at least one of an extract of *Aloe vera* and recombinant human epidermal growth factor.

The composition provides improved pain and discomfort reduction, while promoting healing of the skin. The composition can be used to treat many types of skin burns, including but not limited to sunburns, burns by fire, burns by hot liquids (such as water, steam, and oil), burns by chemical or caustic agents, burns from heat or friction (such as chaffing and branding), and burns by electricity. Furthermore, the composition is suitable for application to various skin areas, including but not limited to the wrist, ankle, hands, feet, fingers, toes, back, shoulders, neck, and face.

DETAILED DESCRIPTION OF EMBODIMENTS

This disclosure describes an improved topical composition for treating skin burns that contains an extract of *Mentha haplocalyx*. *Mentha haplocalyx* is one species in the *Mentha* genus of Mint plants. However, *Mentha haplocalyx* has been found to provide unique benefits that are not provided by other species of the *Mentha* genus, and in particular benefits that are not provided by *Mentha arvensis, Mentha piperita* (commonly-known as peppermint), and *Mentha spicata* (commonly-known as spearmint).

In embodiments, the composition contains a homogenous or substantially-homogenous mixture of an extract of *Mentha haplocalyx* and an extract of *Aloe vera*. Preferably, the *Aloe vera* is *Aloe vera L. var. Chinesis* (Haw.) Berger. The extract of *Aloe vera* may be present in an amount of about 10% to about 20% by volume of the total volume of the composition (% vol/vol). For example, it may be present in an amount of about 11 to about 19% vol/vol, about 12 to about 18% vol/vol, about 13 to about 17% vol/vol, about 14 to about 16% vol/vol, about 10 to about 15% vol/vol, or about 15 to about 20% vol/vol.

In other embodiments, the composition contains a homogenous or substantially-homogenous mixture of an extract of *Mentha haplocalyx*, an extract of *Aloe vera*, and recombinant human epidermal growth factor. Preferably, the *Aloe vera* is *Aloe vera L. var. Chinesis* (Haw) Berger. The recombinant human epidermal growth factor may be commercially-available, such as that sold by Promega. The recombinant human epidermal growth factor may be present in an amount of about 5 μg/mL to about 10 μg/mL. For example, it may be present in an amount of about 6 μg/mL, about 7 μg/mL, about 8 μg/mL, or about 9 μg/mL. The extract of *Mentha haplocalyx* may be present in an amount of about 1 to about 5% vol/vol. For example, it may be present in an amount of about 2% vol/vol, about 3% vol/vol, or about 4% vol/vol.

The composition may be applied to either "broken burned skin" or "intact burned skin." For the purpose of this disclosure, "broken burned skin" means burned skin for which the integrity of the skin has been disrupted. For example, "broken burned skin" encompasses burned skin that contains blisters or open sores. For the purpose of this disclosure, "intact burned skin" means burned skin for which the integrity of the skin has not been disrupted. For example, "intact burned skin" encompasses burned skin that is reddened, swollen, and inflamed, but not blistered. Accordingly, "intact burned skin" generally refers to first degree burns, which are generally limited to the top layer of the skin or tissue and are characterized by redness, pain, and minor swelling, but not blistering. Likewise, "broken burned skin" generally refers to second degree burns, which generally involve the skin or tissue layers beneath the top layer and are characterized by blisters, severe pain, and redness, or third degree burns, which generally involve all of the layers of the skin or tissue as well as underlying tissue.

Embodiments of the composition that are particularly-suitable for treating intact burned skin contain a homogenous or substantially-homogenous mixture of about 10% to about 20% by volume of an extract of *Aloe vera* and an extract of *Mentha haplocalyx*. Preferably, the *Aloe vera* is *Aloe vera L. var. Chinesis* (Haw.) Berger. Embodiments of the composition that are particularly-suitable for treating broken burned skin contain a homogenous or substantially-homogenous mixture of about 1% to about 5% by volume of an extract of *Mentha haplocalyx*, about 5 μg/mL to about 10 μg/mL of recombinant human epidermal growth factor, and an extract of *Aloe vera*. Preferably, the *Aloe vera* is *Aloe vera L. var. Chinesis* (Haw.) Berger.

Because the compositions are applied to skin or tissue of a patient, it is preferred in embodiments that all or some of the components of the composition are sterilized, either individually or together. In embodiments, particularly where the composition may be applied to broker burned skin, it is desired that at least some of the composition be sterile to help prevent infection at the treatment site. Preferably, at least the extract of *Aloe vera* and the recombinant human epidermal growth factor are individually-sterilized before formation of the homogenous mixture. The sterilizing may be performed, for example, by filter sterilization. In embodiments, the extract of *Aloe vera* may be filter sterilized by filtering through a 0.45 µM filter, and the human epidermal growth factor may be filter sterilized by filtering through a 0.22 µM filter.

Any suitable sterilization method or combination of sterilization methods can be used, and can be used on any combination of composition and/or packaging components, as long as the sterilization does not adversely affect the therapeutic effectiveness of the composition. For example, suitable sterilization techniques that may be employed include dry and moist heat sterilization, ionizing radiation (such as electron beam or gamma irradiation), exposure to gas, and aseptic filtration. Any suitable method or combination of methods can be used, and can be used on any combination of composition and/or packaging components, as long as the sterilization does not adversely affect the therapeutic effectiveness of the composition. However, in order to achieve maximum therapeutic effectiveness, the extract of *Aloe vera*, and the recombinant human epidermal growth factor should not be sterilized by heat.

The composition may also contain at least one pharmaceutically-acceptable excipient, such as animal and vegetable fats, oils, waxes, paraffins, starch, tragacanth, a pluronic, cellulose and cellulose derivatives, silicones, bentonites, silicic acid, talc, zinc oxide, aluminum hydroxide, calcium silicates, alginate, acrylate, hyaluronic acid, polyethylene glycol, dimethyl sulfoxide (DMSO), partial glycerides of fatty acids, chitosan, and mixtures thereof. In addition, the composition may contain one or more compounds for improving cosmetic acceptability, including but not limited to, humectants, surfactants, fragrances, coloring agents, emollients, fillers, and the like. Furthermore, the composition may be in the form of, for example, a paste, cream, gel, lotion, powder, spray, aerosol, or liquid. Where one or more of such other additives are present in the composition, and where the other components of the composition are sterilized as described above, it is preferred that the additional additives also be sterilized, so that sterility of the entire composition can be maintained. Such additives can be sterilized by known means, including those described above.

The composition of the disclosure can be prepared in any suitable form, and the form can be tailored for the intended mode of application. For example, as desired, the composition can be made in the form of a cream, a lotion, a liquid, a spray, or the like. In embodiments, a cream or lotion form is desired, as it can be more precisely and easily applied to a treatment site, and can be made to stay in place on the treatment site for a sufficient time to provide a therapeutic effect.

The compositions and methods of the disclosure can be used to treat burned animal tissue. Although the compositions and methods of the disclosure are advantageously used to treat burned skin tissue on a mammal, such as a human, the disclosure is not limited thereto. For example, the compositions and methods can be used to treat other burned tissue besides skin, such as mucous tissue, internal tissue, and the like, and can be used to treat burned tissue on other animals such as domesticated pets, livestock, and the like.

The composition may be applied immediately after burning the skin (e.g., within about 20 to about 30 minutes), shortly after burning the skin e.g., within about 2 to about 4 hours), or some time thereafter (e.g., after about 3 to about 4 days, or longer). Moreover, the composition may be applied to the burned skin a single time, or may be applied to the burned skin multiple times (e.g., at 30 minute intervals for about 5 hours).

Alternatively, if desired, the composition can be applied intermittently for a period of time that generally corresponds to the normal healing time for the particular type of burn. For example, for first degree burns that exhibit a typical healing time of about 2 to about 6 days, the composition can be intermittently applied for up to about 2 to about 6 days. Likewise, for second and third degree burns that exhibit a longer typical healing time depending upon the severity of the burn, the composition can be intermittently applied for a longer period of time.

The composition may be applied so as to at least partially-cover the burned skin. Preferably, the composition can be applied so as to completely cover the burned skin. Optionally, the composition can be applied so as to at least partially-cover unburned skin in the vicinity of the burned skin. For further protection, a covering may be placed over the burned skin. Any suitable covering may be used, and may be tailored to the location, type, and severity of the burn. For example, suitable coverings include bandages, wound dressings, gloves, and the like. In embodiments, the covering may be placed over the burned skin after the composition has been applied to the burned skin. For example, where the burned area is on the hand or fingers, the burned area may be covered with a surgical glove after application of the composition. In other embodiments, the composition may be applied to the covering, which is then applied to the burned skin. For example, the composition may be applied to an adhesive bandage, which is then applied to the burned skin. Preferably, the covering is a material that does not absorb the composition.

EXAMPLE 1

Application to Broken Burned Skin

The skin on Applicant's back was burned by exposure to the sun for approximately six hours, between the hours of about 10 am to about 4 pm. The burned skin was swollen and blistered, and Applicant experienced extreme pain, discomfort and limited movement due to the burned skin for about three days.

After about three days, Applicant applied a topical burn composition that contained a homogenous mixture of an extract of *Aloe vera L. var. Chinesis* (Haw.) Berger, about 5% vol/vol of an extract of *Mentha haplocalyx*, and about 5 µg/mL of recombinant human epidermal growth factor. Prior to formation of the homogenous mixture, the extract of *Aloe vera L. var. Chinesis* (Haw.) Berger was individually-sterilized by filtering through a 0.45 µM filter, and the recombinant human epidermal growth factor was individually-sterilized by filtering through a 0.22 µM filter. The composition was applied so as to completely cover the burned skin, as well as some of the unburned skin in the vicinity of the burned skin. The composition was applied repeatedly at approximately thirty minute intervals for five hours.

Within about four hours, Applicant noticed substantial relief of the pain and swelling associated with the burned skin.

After the five hours, Applicant's back was no longer swollen, Applicant felt no pain, and Applicant's movement was no longer limited.

EXAMPLE 2

Application to Intact Burned Skin

Applicant spilled hot oil on Applicant's wrist, hands, and fingers. The burned skin was reddened, swollen, and Applicant experienced extreme pain and discomfort due to the burned skin.

Within about 20 minutes, Applicant applied a topical burn composition that contained 100% by volume of an extract of *Mentha haplocalyx*. The composition was applied so as to completely cover the burned skin, as well as some of the unburned skin in the vicinity of the burned skin. The burned skin was then covered with a surgical glove.

Within about two hours, Applicant noticed a complete absence of the pain, discomfort, swelling, and redness associated with the burned skin.

While the disclosure above contains various embodiments and examples, it is evident that many alternatives, modifications, and variations will be apparent to those skilled in the art. Accordingly, the embodiments and examples are intended to be illustrative and not limiting. Various changes may be made without departing from the spirit and scope of the disclosure.

What is claimed is:

1. A topical burn composition, comprising an extract of *Mentha haplocalyx* and at least one of an extract of *Aloe vera* and recombinant human epidermal growth factor.

2. The topical burn composition of claim 1, comprising the extract of *Mentha haplocalyx* and the extract of *Aloe vera*.

3. The topical burn composition of claim 1, comprising the extract of *Mentha haplocalyx*, the extract of *Aloe vera*, and the recombinant human epidermal growth factor.

4. The composition of claim 1, comprising an extract of *Aloe vera L. var. Chinesis (Haw.) Berger*.

5. The composition of claim 1, comprising about 1 to about 5% vol/vol of the extract of *Mentha haplocalyx*.

6. The composition of claim 1, comprising about 10 to about 20% vol/vol of the extract of *Aloe vera*.

7. The composition of claim 1, comprising about 5 to about 10 μg/mL of the recombinant human epidermal growth factor.

8. The composition of claim 1, comprising a homogenous mixture of the extract of *Mentha haplocalyx* and about 10 to about 20% vol/vol of the extract of *Aloe vera L. var. Chinesis (Haw.) Berger*.

9. The composition of claim 8, comprising about 15%vol/vol of the extract of *Aloe vera L. var. Chinesis (Haw.) Berger*.

10. The composition of claim 1, comprising a homogenous mixture of an extract of *Aloe vera L. var. Chinesis (Haw.) Berger*, about 1 to about 5% vol/vol of the extract of *Mentha haplocalyx*, and about 5 to about 10 μg/mL of the recombinant human epidermal growth factor.

11. The composition of claim 10, comprising about 5% vol/vol of the extract of *Mentha haplocalyx* and about 5 μg/mL of the recombinant human epidermal growth factor.

12. The composition of claim 1, further comprising at least one member selected from the group consisting of excipients, humectants, surfactants, fragrances, coloring agents, emollients, and fillers.

13. A method of treating burned skin, comprising applying the composition of claim 1 to the burned skin to completely cover the burned skin.

14. A method of treating burned skin, comprising applying the composition of claim 8 to intact burned skin.

15. A method of treating burned skin, comprising applying the composition of claim 10 to broken burned skin.

16. The method of claim 13, further comprising covering the burned skin with a material that does not absorb the composition.

17. The method of claim 16, comprising covering the burned skin after application of the composition.

18. The method of claim 16, comprising applying the composition to the material, and applying the material to the burned skin.

19. The topical burn composition of claim 1, comprising about 1 to about 5% vol/vol of the extract of *Mentha haplocalyx* and at least one of about 10 to about 20% vol/vol of the extract of *Aloe vera* and about 5 to about 10 μg/mL of the recombinant human epidermal growth factor.

* * * * *